United States Patent
Hochtritt et al.

(10) Patent No.: US 10,687,995 B2
(45) Date of Patent: Jun. 23, 2020

(54) FOLDED ABSORBENT SHEET PRODUCTS DISPENSER HAVING INTERCHANGEABLE DISPLAY FEATURE, AND METHODS OF USING AND MARKETING SAME

(75) Inventors: Robert C. Hochtritt, Neenah, WI (US); Andrew Conger, Neenah, WI (US)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 2905 days.

(21) Appl. No.: 10/938,527

(22) Filed: Sep. 13, 2004

(65) Prior Publication Data

US 2005/0087541 A1    Apr. 28, 2005

Related U.S. Application Data

(60) Provisional application No. 60/514,600, filed on Oct. 28, 2003.

(51) Int. Cl.
*A61F 15/00* (2006.01)
*A61F 13/551* (2006.01)

(52) U.S. Cl.
CPC .......... *A61F 15/001* (2013.01); *A61F 13/551* (2013.01)

(58) Field of Classification Search
CPC .............................. A61F 15/001; A61F 13/551
See application file for complete search history.

(56) References Cited

U.S. PATENT DOCUMENTS

| | | | |
|---|---|---|---|
| 777,082 A | | 12/1904 | Cutler |
| 2,354,058 A | * | 7/1944 | Redfield .................. 242/564.4 |
| 3,028,047 A | * | 4/1962 | Tuft ............................... 221/44 |
| 3,674,175 A | * | 7/1972 | Jaquish ......................... 221/92 |
| 3,979,020 A | | 9/1976 | Braber et al. |
| 4,143,792 A | * | 3/1979 | Rex ............................... 221/97 |
| 4,413,749 A | * | 11/1983 | Glaser ............................ 221/1 |
| 4,919,377 A | * | 4/1990 | Alexander et al. ...... 248/223.41 |
| 5,011,010 A | * | 4/1991 | Francis et al. ............... 206/307 |
| 5,082,229 A | * | 1/1992 | Dahl ......................... 248/444.1 |

(Continued)

FOREIGN PATENT DOCUMENTS

GB    2357080 A  *  6/2001  ........... B65D 5/4801

OTHER PUBLICATIONS

Janet Beighle-French, New Products Ease Home Frustrations, Nov. 11, 1996, The Plain Dealer, Cleveland Ohio, p. 7D.*

(Continued)

*Primary Examiner* — Colleen A Hoar
(74) *Attorney, Agent, or Firm* — Faegre Drinker Biddle & Reath LLP

(57) ABSTRACT

A dispenser for absorbent sheet products includes a transparent cover that permits opening the dispenser body so as to load folded absorbent sheet products therein. The dispenser also includes a lower opening such that absorbent sheet products can be withdrawn therefrom, either one-by-one and/or in groups, while the transparent cover is in a closed position. The transparent cover has a plurality of tabs or rails located on an interior surface thereof. The tabs or rails are adapted to receive and retain an inserted sheet of printed material pressed against the inner surface of the transparent cover. The dispenser and/or the absorbent sheet products are able to be customizable for marketing purposes.

4 Claims, 1 Drawing Sheet

(56) References Cited

U.S. PATENT DOCUMENTS

| | | | | |
|---|---|---|---|---|
| 5,102,007 | A * | 4/1992 | Petterson | A47K 10/425 221/33 |
| 5,123,566 | A * | 6/1992 | Lege et al. | 221/46 |
| 5,131,561 | A | 7/1992 | Casperson et al. | |
| 5,190,186 | A * | 3/1993 | Yablans et al. | 221/124 |
| 5,261,557 | A * | 11/1993 | Bytell et al. | 220/662 |
| 5,269,409 | A * | 12/1993 | Brandt et al. | 206/303 |
| 5,356,032 | A * | 10/1994 | Rhodes | 221/47 |
| 5,515,999 | A * | 5/1996 | Jo | G11B 23/0236 221/45 |
| 5,535,320 | A * | 7/1996 | Gay | G06T 11/60 715/234 |
| 5,678,728 | A * | 10/1997 | Leto | 221/185 |
| 5,690,230 | A * | 11/1997 | Griffith | 206/555 |
| 5,743,605 | A * | 4/1998 | Marino | 312/211 |
| 5,813,569 | A * | 9/1998 | Cihanek | 221/150 R |
| 5,823,344 | A * | 10/1998 | Fantone et al. | 206/459.5 |
| 5,823,353 | A * | 10/1998 | Perrin et al. | 206/752 |
| 5,857,791 | A | 1/1999 | Kenney | |
| 5,865,340 | A * | 2/1999 | Alvern | 221/13 |
| 5,894,931 | A * | 4/1999 | Dunn | 206/555 |
| 6,056,133 | A * | 5/2000 | Luenser | 211/183 |
| 6,145,231 | A * | 11/2000 | Valiulis | 40/661.03 |
| 6,386,389 | B1 | 5/2002 | Percy et al. | |
| 6,427,838 | B1 * | 8/2002 | Fulda | 206/455 |
| 6,519,885 | B2 * | 2/2003 | Valiulis | 40/661.03 |
| 6,705,473 | B1 * | 3/2004 | Schlesinger | 211/50 |
| 6,726,014 | B2 * | 4/2004 | Laurent | 206/494 |
| 6,871,755 | B2 * | 3/2005 | DeVries et al. | 221/7 |
| 6,964,349 | B2 * | 11/2005 | Sears et al. | 221/48 |
| 2006/0076357 | A1 * | 4/2006 | Braat et al. | 221/34 |
| 2006/0102642 | A1 * | 5/2006 | Muntzing et al. | 221/45 |

OTHER PUBLICATIONS

Plasticrafters Website, Jan. 11, 2002, p. 1-2.*
Joel Palmer, Rolling Meadows parks pursues deal with Pepsi Bottler, Sep. 24, 1997, Chicago Daily Herald, News; p. 4.*

* cited by examiner

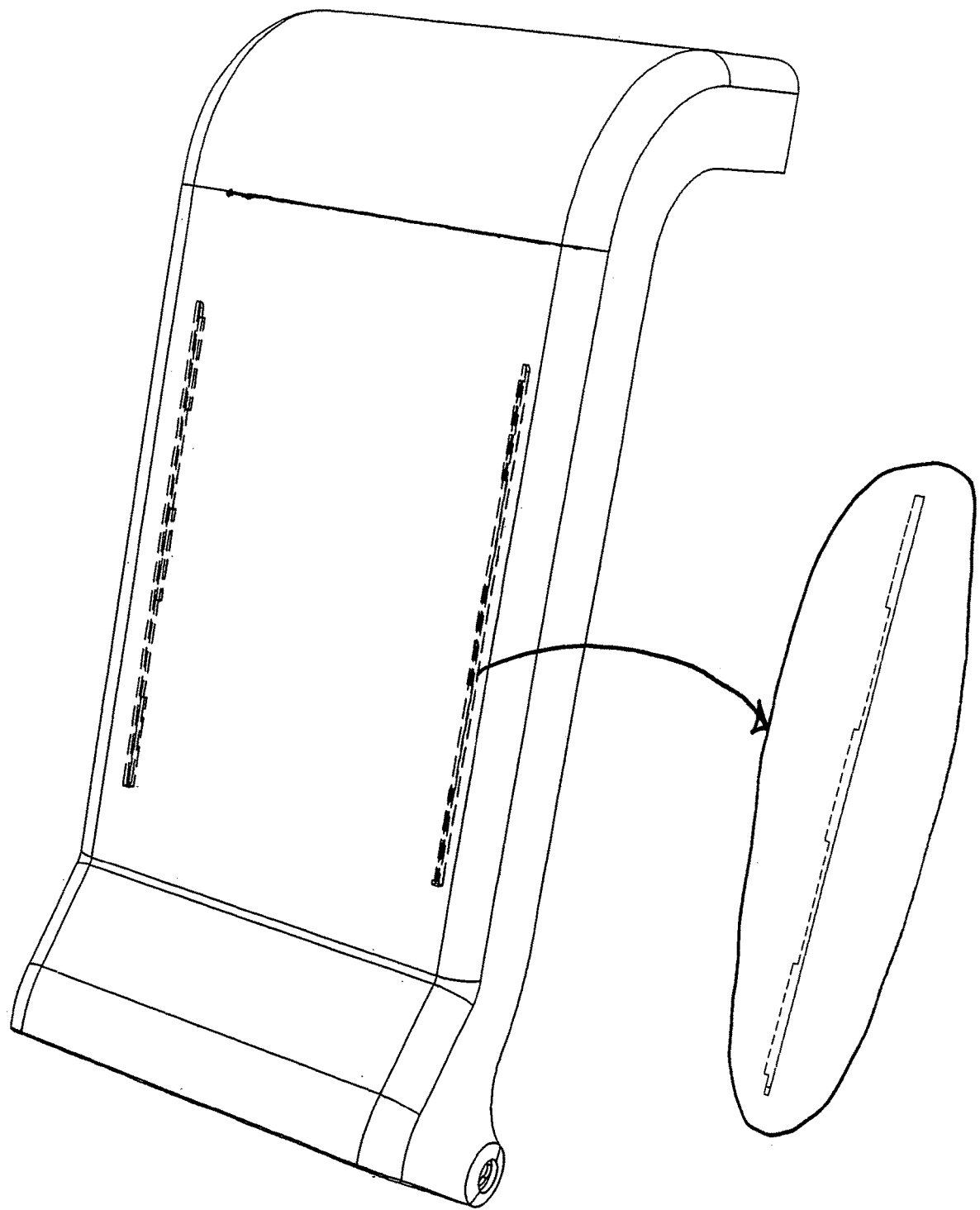

FOLDED ABSORBENT SHEET PRODUCTS DISPENSER HAVING INTERCHANGEABLE DISPLAY FEATURE, AND METHODS OF USING AND MARKETING SAME

CROSS REFERENCE TO RELATED APPLICATIONS

This application claims the 35 USC 119(e) benefit of prior U.S. Provisional application No. 60/514,600 filed on Oct. 28, 2003.

This application is also related to the disclosure of one U.S. design patent application and three regular U.S. utility patent applications, all filed in the U.S. Patent and Trademark Office on Sep. 12, 2003, each naming Robert C. Hochtritt and Andrew M. Conger as inventors, the serial numbers of those application Ser. Nos. 29/189,877, 10/660,659, 10/660,656 and 10/660,694. The entirety of those four applications, including the drawings thereof, is hereby expressly incorporated by reference.

SUMMARY OF THE INVENTION

An improvement to the dispensers for absorbent sheet products as described in those applications comprises providing a set of tabs or rails on inner surfaces of the transparent cover, which tabs or rails are spaced and dimensioned so as to retain a sheet of paper pressed against the inside of the transparent cover, which sheet is thereby viewable from outside of the dispenser when the cover is closed.

The purpose of that additional structure is to permit the management of an establishment in which the dispenser is present, to provide a changeable display that takes advantage of the transparency of the dispenser cover.

BRIEF DESCRIPTION OF THE DRAWING

The attached FIG. 1 shows in broken lines the approximate shape and location of the tabs or rails according to one possible embodiment of the invention.

DETAILED DESCRIPTION OF THE PREFERRED EMBODIMENT

In particular, the broken lines in FIG. 1 illustrate the possible lateral outlines of a sheet to be inserted, with tabs or rails existing along part or all of that outline. It will be appreciated that the number and spacing of such tabs or rails can be varied as a matter of design choice, and as a function of the stiffness of the paper to be inserted, so that the paper is maintained pressed against the inside of the transparent cover as much as desired.

The tabs or rails according to the invention are preferably defined by the mold from which the transparent cover is produced, such that they are formed integrally with the transparent cover. However, alternatively, the tabs could be separately provided, and attached for example by gluing or welding.

The broken lines in FIG. 1 are intended to reflect an insert sheet of approximately conventional letter size, i.e., 8½ by 11 inches. However, the width and height of the space defined by the tabs can be varied at will, to accommodate insert sheets of different sizes. For example, and without limitation, insert sheets of A4 size could be provided, as well as substantially smaller insert sheets, e.g. of 3 by 5 inch card size.

Preferably, the size of the insert sheet is somewhat less than the full width and height of the transparent cover, so that, even with an insert sheet in position, the quantity of folded absorbent sheet products remaining in the dispenser can be observed.

It may also be desired to position the tabs and rails so as to accommodate a sheet of non-standard size, e.g. 8 by 9 inches, which would permit the manufacturer or seller of the dispenser to sell to its customer not only the dispenser but also the non-standard size sheet material for use in the interchangeable display feature.

In another aspect of the invention, the dispenser is provided together with software containing templates for generating printed graphics on the sheets to be inserted into the tabs and/or rails of the dispenser cover. In a relatively simple form, such software could take the form of a pre-recorded CD-ROM or any other computer readable medium, containing a set of template files each including a predetermined border and/or background pattern, which template files can be modified by the end user to include custom information pertinent to the user's particular display. Thus, the software aspect of the invention could consist of a CD-ROM or other computer readable medium containing a group of such graphic files which can be opened into commercially available word processing programs, e.g. Microsoft Word or WordPerfect.

An advantage of the present invention is in the expectation that it will improve marketability of dispensers for folded absorbent sheet products, and, in turn, the ability to increase sales volume of absorbent sheet products to be used in such dispensers. This advantage of the invention will be more significant in the case wherein the manufacturer and/or seller of the dispenser also is in the business of selling absorbent sheet products for use in the dispenser. In that case, it is not uncommon for such sellers to generate a significant proportion of their revenues from sale of absorbent sheet products; moreover, in some cases a purchaser of a given dispenser will in practice purchase absorbent sheet products for use in that dispenser from the same commercial entity from which the dispenser was purchased.

Consequently, another aspect of the invention pertains to a method of marketing absorbent sheet products dispensers and/or absorbent sheet products for use in such dispensers, comprising supplying to a purchaser of absorbent sheet products dispensers and absorbent sheet products for use therein, at least one absorbent sheet products dispenser having a transparent cover or portion with tabs and/or rails formed on an inner surface thereof, for accommodating a printed sheet that can be interchanged at a frequency selected by the dispenser purchaser. The dispenser may moreover be provided to the purchaser together with software for use in generating customized printed graphic sheets for insertion within the tabs and/or rails of the dispenser cover. Such software may be supplied simultaneously with the dispenser as a package, or may be supplied separately therefrom and spaced in time, either preceding delivery of the dispenser, or subsequently.

The present invention has been described with reference to particular embodiments. However, the invention should not be restricted to those embodiments, but only to the appended claims. It is to be appreciated by those having ordinary skill in the art that changes or modifications to the embodiments can be made without departing from the scope and spirit of the invention.

What is claimed is:

1. A dispenser for absorbent sheet products comprising:
a plurality of walls defining an interior of the dispenser for enclosing a stack of the absorbent sheet products;
a plurality of tabs or rails connected to one of said plurality of walls,
wherein:
at least one of said plurality of walls has an opening configured to allow withdrawal of the absorbent sheet products, from said interior of the dispenser, one-by-one,
at least one of said plurality of walls is transparent and includes an interior surface partly defining said interior of the dispenser,
said plurality of tabs or rails extend directly from said interior surface and are configured to receive and retain a sheet of paper pressed against said interior surface, and
said plurality of tabs or rails are spaced from one another so as to define an area smaller than a total transparent area of said at least one transparent wall, to thereby permit viewing there through of a remaining quantity of absorbent sheet products in said interior of the dispenser.

2. The dispenser of claim 1, wherein said at least one transparent wall and said at least one wall including said opening are two separate walls of said plurality of walls.

3. The dispenser of claim 2, wherein said at least one transparent wall and said at least one wall including said opening are directly connected to one another.

4. A system comprising:
the dispenser of claim 1; and
software associated with said dispenser and configured to generate customizable printed inserts to be received and retained by said plurality of tabs or rails.

* * * * *